US010811132B1

(12) United States Patent
Shenoy et al.

(10) Patent No.: US 10,811,132 B1
(45) Date of Patent: Oct. 20, 2020

(54) SYSTEM AND METHOD FOR INTEGRATING NUTRITIONAL INFORMATION WITH TRANSACTIONAL DATA

(71) Applicant: JPMorgan Chase Bank, N.A., New York, NY (US)

(72) Inventors: Prasad N. Shenoy, Rutherford, NJ (US); Antonino Cummings, Austin, TX (US); Johanna L. Cohen, New Paltz, NY (US)

(73) Assignee: JPMORGAN CHASE BANK, N.A., New York, NY (US)

( * ) Notice: Subject to any disclaimer, the term of this patent is extended or adjusted under 35 U.S.C. 154(b) by 451 days.

(21) Appl. No.: 15/346,898

(22) Filed: Nov. 9, 2016

Related U.S. Application Data

(63) Continuation-in-part of application No. 14/882,071, filed on Oct. 13, 2015, now Pat. No. 10,628,824.

(51) Int. Cl.
*G16H 20/60* (2018.01)
*H04L 29/06* (2006.01)
*G06Q 30/02* (2012.01)

(52) U.S. Cl.
CPC ............ *G16H 20/60* (2018.01); *G06Q 30/02* (2013.01); *H04L 63/102* (2013.01)

(58) Field of Classification Search
None
See application file for complete search history.

(56) References Cited

U.S. PATENT DOCUMENTS 6,456,984 B1 * 9/2002 Demoff ................ G06Q 20/02
705/38
8,452,658 B2 5/2013 Urbanski
(Continued)

FOREIGN PATENT DOCUMENTS

WO WO-2017023555 A1 * 2/2017 ............ G06F 3/167

OTHER PUBLICATIONS

Simone A. French et al., Annotated receipts capture household food purchases from a broad range of sources, Int'l J. of Behavioral Nutrition and Physical Activity 6:37 (2009), https://www.ncbi.nlm.nih.gov/pmc/articles/PMC2714491/pdf/1479-5868-6-37.pdf (last visited Jun. 11, 2020) (Year: 2009).*
(Continued)

*Primary Examiner* — John P Go
*Assistant Examiner* — Nicholas Akogyeram, II
(74) *Attorney, Agent, or Firm* — Greenblum & Bernstein, P.L.C.

(57) ABSTRACT

A method is provided for monitoring and communicating nutritional data to end user devices. The method comprises receiving data from external sources including merchant systems distributing items having nutritional value and a third party aggregator system storing nutritional information for the distributed items. The method further includes storing instructions and databases in at least one computer memory, the databases including a receipts database storing receipts transmitted from the merchant systems, wherein the receipts include an identification of the distributed items. The method additionally includes calling an application program interface of the aggregator system and providing data from identified receipts including identification of distributed items and receiving nutrition information for the distributed items from the aggregator service. The method further includes parsing the received nutrition information (Continued)

and storing the parsed nutrition information in a customer database stored in the computer memory for communication to the end user devices.

14 Claims, 6 Drawing Sheets

(56) References Cited

U.S. PATENT DOCUMENTS

| | | |
|---|---|---|
| 2006/0253578 A1 | 11/2006 | Dixon et al. |
| 2007/0299920 A1* | 12/2007 | Crespo ............... G06Q 30/0603 709/206 |
| 2008/0034001 A1* | 2/2008 | Noel ..................... G06Q 10/00 |
| 2009/0063332 A1* | 3/2009 | Tabaczynski .......... G06Q 20/10 705/39 |
| 2009/0171749 A1 | 7/2009 | Laruelle et al. |
| 2012/0083669 A1* | 4/2012 | Abujbara ............ G06F 19/3475 600/300 |
| 2013/0253986 A1 | 9/2013 | Urbanski |
| 2015/0032586 A1* | 1/2015 | Blackhurst ......... G06Q 30/0631 705/35 |
| 2016/0188563 A1* | 6/2016 | Radcliffe .............. G06F 40/205 704/239 |
| 2017/0039886 A1* | 2/2017 | Bitran ................... G06F 3/0482 |

OTHER PUBLICATIONS

PCT International Search Report dated Jan. 10, 2017.

* cited by examiner

SYSTEM AND METHOD FOR INTEGRATING NUTRITIONAL INFORMATION WITH TRANSACTIONAL DATA

RELATED APPLICATION

This application is a continuation-in-part application of U.S. patent application Ser. No. 14/882,071, filed on Oct. 13, 2015. This application incorporates by reference and claims priority to the above-noted earlier filed application.

FIELD OF THE INVENTION

Embodiments of the present invention are generally related to systems and methods for obtaining and utilizing nutrition information based on transactional data.

BACKGROUND OF THE INVENTION

With the proliferation of online systems and wearable and mobile-based systems for tracking health and fitness goals, society has seen an increased focus on monitoring and tracking food consumption. In addition to the health monitoring devices, such as Fitbit™, Garmin™, Polar™, and others, mobile applications, or "apps," with fitness goal tracking capabilities have become popular for use on smartphones, tablets, and other mobile devices. Like applications that execute on traditional computing devices, apps allow users to perform a wide range of actions. Fitness trackers, such as Fitbit™, which is usable on a mobile device, allows tracking of calories consumed, tracking of weight gain and loss and recording of health information such as blood pressure and glucose levels. Apps such as Lose It™ and MyFitnessPal™ help users to track fitness goals. Websites such as Mydailyplate.com, (now acquired by Livestrong.com) provide similar functionality.

Given the ongoing concern with obesity in the United States, people are becoming increasingly health conscious. However, consumers tend to lose track of calories consumed, particularly when eating at restaurants. Thus, a problem arising with existing apps and devices is that users fail to follow through with their goals due to the manual nature of nutrition tracking. Users are required to manually enter information regarding caloric intake. Some existing systems may require users to look up and enter nutrition information based on daily consumption. Others may consult databases for nutrition information, but nonetheless require user input to perform the lookup and verification. Thus, most users fall short of their fitness goals when using such systems because they are required to search for and verify the correct restaurants and food items and enter the quantity consumed manually.

Generally, most users of these fitness systems purchase the food they consume either at a restaurant or a grocery store. Thus, a record exists of the food items actually purchased by the user. For example, the system disclosed in U.S. patent application Ser. No. 14/882,071 includes an enterprise system that receives receipts from third party systems including purchase data. For example, the enterprise may be a financial institution and third party systems may be or include a vendor, distributor, reseller, or any other entity that provides a good or service to a customer. The enterprise receives detailed transaction details including itemized receipts from the third party systems.

Systems also exist for storing nutrition information for popular food items. For example, websites such as Calorieking™ store nutrition information for items on restaurant menus categorized by restaurant. Such systems also offer nutrition information based on food category, such as fruit, vegetable, grain, meat, dairy, etc.

Unfortunately, no current system exists for integrating these existing tools to help users meet fitness goals while reducing the burden of excessive manual user input. Further, no currently existing system allows users to receive recommendations of items for consumption based on available data. Accordingly, a goal of the presently disclosed system is to enhance the probability that users of existing systems will meet fitness goals by integrating transactional data and nutrition information, thereby reducing the requirement for manual user input.

SUMMARY OF THE INVENTION

Embodiments of the invention provide functionality for integrating transaction data and nutrition information to enable automatic delivery of nutritional information to system users.

In an embodiment of the invention, a computing system is provided for monitoring and communicating nutritional data to end user devices. The system includes at least one communication interface for receiving data from external sources including merchant systems distributing items having nutritional value and third party aggregator systems storing nutritional information for the distributed items. The system further includes at least one computer memory storing instructions and databases including a receipts database storing receipts transmitted from the merchant systems. Each receipt includes an identification of one or more distributed items associated with a customer operating an end user device. The system includes a computer processor performing multiple steps including calling an application program interface of the aggregator system and providing data from receipts including identification of distributed items, receiving nutrition information for the distributed items from the aggregator system, and parsing the received nutrition information. The system further stores the parsed nutrition information in a customer database for communication to the end user devices.

In further embodiments of the invention, a method is provided for monitoring and communicating nutritional data to end user devices. The method includes receiving data from external sources including merchant systems distributing items having nutritional value and a third party aggregator system storing nutritional information for the distributed items. The method additionally includes storing instructions and databases in at least one computer memory, the databases including a receipts database storing receipts transmitted from the merchant systems, each receipt including an identification of the distributed items and associated with a customer operating an end user device. The method additionally includes calling an application program interface of the aggregator system and providing data from identified receipts including identification of distributed items. The method further includes receiving nutrition information for the distributed items from the aggregator system, parsing the received nutrition information, and storing the parsed nutrition information in a customer database stored in the computer memory for communication to the end user devices.

In yet an additional embodiment of the invention, a computer-readable medium stores instructions executed by a computer processor to perform multiple steps. The steps include receiving data from external sources including merchant systems distributing items having nutritional value and a third party aggregator system storing nutritional information for the distributed items and storing instructions and databases in at least one computer memory, the databases including a receipts database storing receipts transmitted from the merchant systems. The steps additionally include calling an application program interface of the nutrition aggregator system, providing data from identified receipts including identification of distributed items, receiving nutrition information for the distributed items from the aggregator system, parsing the received nutrition information, and storing the parsed nutrition information in a customer database stored in the computer memory for communication to the end user devices.

BRIEF DESCRIPTION OF THE DRAWINGS

In order to facilitate a fuller understanding of the present invention, reference is now made to the accompanying drawings, in which like elements are referenced with like numerals. These drawings should not be construed as limiting the present invention, but are intended to be exemplary only.

DETAILED DESCRIPTION OF THE INVENTION

Embodiments of the presently disclosed invention provide a method and system for monitoring nutrition information for end users and communicating the information to the end users in an optimized manner.

Figure 1A:
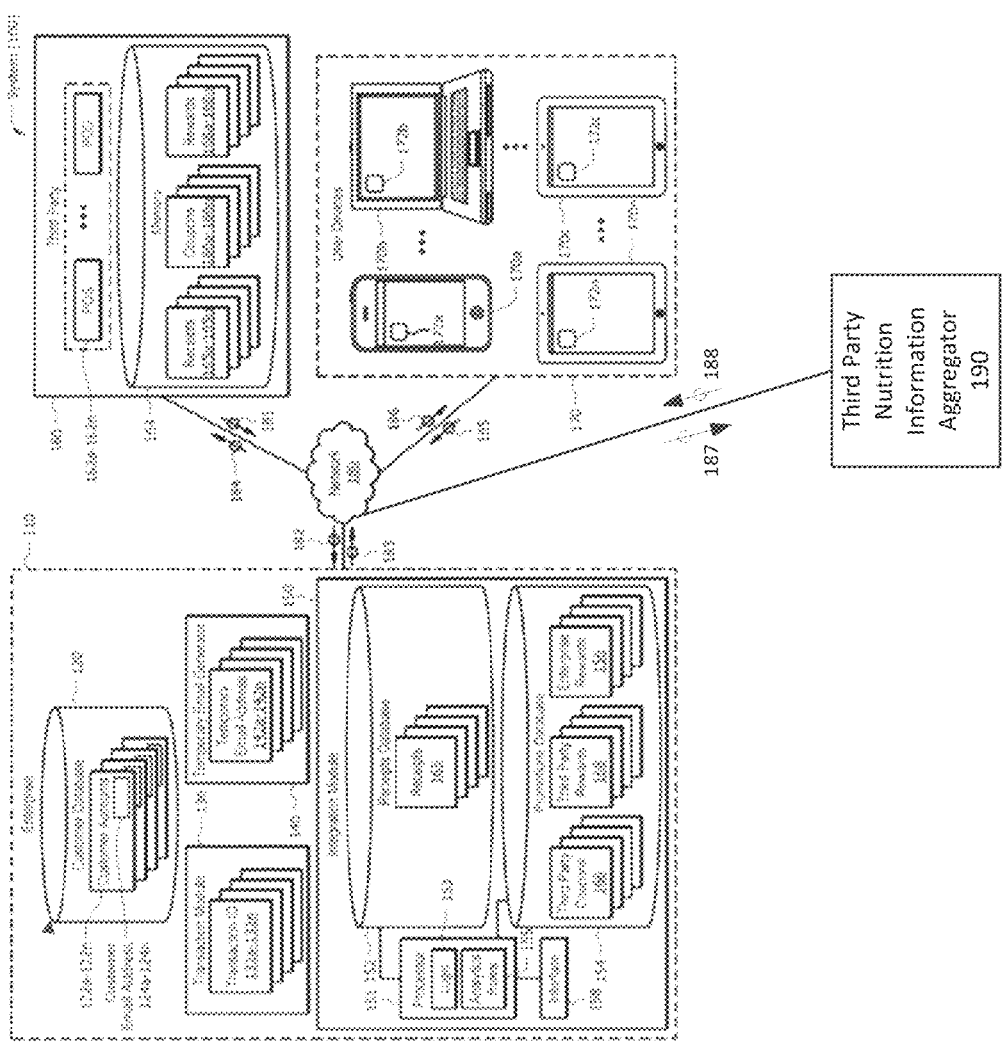
FIG. 1A is a block diagram illustrating an operating environment including a system for providing nutrition information based on purchase information in accordance with an embodiment of the invention.

FIG. 1A is a block diagram illustrating an exemplary embodiment of a nutrition tracking system in accordance with an embodiment of the invention. System 100 includes enterprise 110. Enterprise 110 is connected over one or more networks 180 with a third party system 160 that provides consumables having nutritional value, end user devices 170, and a third party nutrition aggregator system 190 that stores nutritional information.

Enterprise 110 may be an organization (e.g., a financial institution) that includes business units, divisions, or lines of businesses that handle the trade of various goods and services within the enterprise. Enterprise 110 of system 100 may have one or more customers, wherein the enterprise's customers may comprise individuals, entities, or a combination thereof. In the illustrated embodiment of FIG. 1, enterprise 110 comprises customer database 120, transaction module 130, temporary email generator 140, and integration module 150. Generally, customer database 120, transaction module 130, temporary email generator 140, and integration module 150 interact to efficiently analyze and communicate customer data.

In the illustrated embodiment of FIG. 1A, customer database 120 stores customer accounts 122. Customer accounts 122a-122n represent the accounts a customer holds with enterprise 110, wherein n represents any suitable number. Customer account 122 may comprise one or more accounts held by a customer of enterprise 110. For example, customer account 122a may represent a personal checking account, savings account, credit card account, or investment account (e.g., money market deposit account). As another example, customer account 122b may represent an entity's commercial banking account (e.g., a small business checking account or a corporate account). Customer account 122 may include customer email addresses 124a-124n. For example, customer account 122a held by a particular customer of enterprise 110 may comprise that particular customer's email address. As another example, customer account 122a held by a particular customer of enterprise 110 may comprise multiple email addresses associated with that particular customer. As will further be described below with respect to FIG. 1B, the customer record may additionally store nutrition information relevant to customer purchases.

The illustrated embodiment of FIG. 1A further comprises transaction module 130. Transaction module 130 is operable to receive a request from third party 160 to authorize a transaction. The transaction represents any transfer or exchange of goods, services, and/or funds between enterprise 110 and third party 160. Third party 160 may be any entity external to the enterprise. For example, enterprise 110 may be a financial institution and third party 160 may be a vendor, distributor, reseller, or any other entity that provides a good or service to a customer. In embodiments of the invention, the third party system 160 belongs to a vendor of consumable items such as food and drink. For example, the third party may be a restaurant, grocery store, or convenience store.

Third party 160 may comprise points-of-sale 162a-162n, wherein n represents any suitable number. Point-of-sale 162 may comprise a device in a store of third party 160 or any other device that facilitates customer transactions. As shown in the illustrated embodiment, third party 160 further comprises memory 164 operable to store one or more transaction receipts 165a-165n and/or promotions. A transaction receipt (e.g., transaction receipt 165a) is any acknowledgment of the transaction. In the illustrated embodiment of FIG. 1A, transaction receipt 165 represents an electronic acknowledgment. A promotion is something given to a customer to raise customer awareness of a product, brand or service, to create brand loyalty, and/or to generate sales. In the illustrated embodiment, promotions comprise coupons 166 and/or rewards 168. As shown in FIG. 1A, transaction receipts 165a-165n, coupons 166a-166n, and rewards 168a-168n are associated with third party 160. A coupon (e.g., coupon 166a) may entitle a customer of third party 160 to a discount for a particular product or service, and a reward (e.g., reward 168a) may be given by third party 160 to a customer in recognition of the customer's behavior. For example, third party 160 may give a customer of third party 160 a reward for every dollar spent at third party 160's store. Coupons 166 and rewards 168 may be given to incentivize customers of third party 160 to continue a business relationship with third party 160 or to maintain their loyalty to third party 160.

Nutrition information aggregation system 190 may be or include a nutrition aggregator, such as Calorie King™ or other system that collects nutrition information with respect to multiple categories of foods from multiple restaurants and stores that information in a central repository. In some embodiments, the third party systems 160 may store nutrition information pertaining to the particular items that they sell. In this instance, the enterprise system 110 may additionally or alternatively interact with the third party systems 160 to collect nutrition information.

Transaction module 130 of system 100 is further operable to authorize a transaction between a customer of enterprise 110 and third party 160. Customer of enterprise 110 may also be a customer of third party 160. In certain embodiments, transaction module 130 receives a request to authorize a transaction from third party 160 prior to authorizing the transaction. For example, a customer of enterprise 110 may attempt to purchase an item from third party 160 by swiping a debit card associated with customer account 122 at point-of-sale device 162. Third party 160 communicates with enterprise 110 requesting authorization of the purchase transaction. After verifying customer account 122 is adequately funded to cover the purchase transaction, enterprise 110 may authorize the transaction.

After authorizing the transaction, transaction module 130 of system 100 generates transaction identifier 132, as illustrated in FIG. 1. Transaction identifier 132 represents a string of characters that identifies the transaction. In some embodiments, transaction identifier 132 is a unique, temporary identifier that expires after a certain amount of time once the transaction is completed. For example, transaction identifier 132 may expire two hours once the transaction is completed and may be recycled and used again at a later time to identify a different authorized transaction. In certain embodiments, enterprise 110 associates transaction identifier 132 with the customer associated with the transaction. In the event that transaction identifier 132 expires, enterprise 110 may not associate transaction identifier 132 with the customer associated with the transaction. In some embodiments, transaction module 130 is further operable to process and complete the transaction and communicate the completed transaction to third party 160.

System 100, as shown in the illustrated embodiment of FIG. 1, further comprises temporary email generator 140. Temporary email generator 140 of system 100 generates temporary email addresses 142a-142n. For example, temporary email generator 140 of system 100 may generate temporary email address 142a for a transaction in response to generated transaction identifier 132a. Temporary email address 142 may be based on transaction identifier 132. For example, transaction module 130 may generate transaction identifier 132a that is represented as "123abc456," and temporary email generator may generate temporary email address 142a based on transaction identifier 132a, wherein temporary email address 142a is represented as 123abc456@domain.com.

Temporary email generator 140 of system 100 is further operable to link a temporary email address to an email address of a customer of enterprise 110. For example, temporary email generator 140 may link temporary email address 142a to customer email address 124a. In certain embodiments, temporary email generator 140 maps the temporary email address to an email address of a customer of enterprise 110. Mapping may comprise redirecting email sent to a temporary email address (e.g., temporary email address 142a) to the customer's email address (e.g., customer email address 124a). In some embodiments, temporary email generator 140 forwards emails received by a temporary email address to an email address of a customer of enterprise 110. In an embodiment, temporary email generator 140 automatically forwards emails received by temporary email address 142a to customer email address 124a.

In certain embodiments, temporary email generator 140 of system 100 communicates a temporary email address to third party 160. In some instances, temporary email generator 140 automatically communicates the temporary email address to third party 160. For example, temporary email generator 140 may automatically communicate temporary email address 142a to third party 160 in response to the generation of temporary email address 142a by temporary email generator 140. In some embodiments, temporary email generator 140 only communicates temporary email address 142a to third party 160 upon a request by third party 160 for a temporary email address.

Integration module 150 represents a component that facilitates the integration of transaction information from multiple third parties 160. In the illustrated embodiment, integration module 150 includes one or more processors 151, one or more interfaces 158, receipts database 152, and promotions database 154. As shown in the illustrated embodiment, processor 151 includes logic 153 and analytics/rules 155. Interface 158 of integration module 150 is operable to receive transaction information from third party 160. In certain embodiments, integration module 150 receives transaction information electronically.

Integration module 150, as illustrated in FIG. 1, may store transaction information in receipts database 152 and/or promotions database 154. Transaction information may comprise receipts 165a-165n received from third party 160, where n represents any suitable number. A transaction receipt is an acknowledgment of a transaction, such as a purchase transaction between third party 160 and a customer of enterprise 110. For example, integration module 150 may electronically receive transaction receipt 165a from third party 160 and store transaction receipt 165a in receipts database 152, wherein transaction receipt 165a comprises an acknowledgement of a purchase by a customer from third party 160. In certain instances, the customer of third party 160 is also a customer of enterprise 110.

In some embodiments, integration module 150 may receive a request to access transaction receipt 165a from user device 170. User devices 170 may include any suitable computing device that may be used to access one or more applications 172 through network 180. User devices 170 may include mobile computing devices with wireless network connection capabilities (e.g., wireless-fidelity (WI-FI), and/or BLUETOOTH capabilities). For example, user devices 170 may include smartphones, laptop computers, or tablet computers (such as smartphone 170a, laptop 170b, and tablet 170c). The user mobile devices 170 may include handheld devices including mobile smartphones, such as Android® phones and iPhones®, tablets, or hand-held wireless devices such as PDAs, multiprocessor systems, microprocessor-based or programmable consumer electronics, minicomputers, other handheld devices that may now be available or may in the future become available. These mobile devices 170 may utilize downloadable mobile applications as will be further described below. User devices 170 may also include non-mobile devices such as desktop computers. In certain embodiments, a number of different user devices 170 may be associated with a particular user. For example, a particular user may own each of smartphone 170a, laptop 170b, and tablet 170c, and may use such devices to access the one or more applications 172 as described herein.

The application 172, may in embodiments of the invention, be an application provided by the enterprise 110. For example, if the enterprise 110 is a financial institution, the mobile application 172 may be a banking mobile app. However, the mobile application 172 may have additional functionality, such as nutrition tracking functionality as is further explained herein. Further, mobile applications 172 may operate in conjunction with hardware for tracking calories burned and also for retrieving stored user fitness goals and calculating a remaining amount of calories available to the user based on the retrieved nutrition information and calories burned. The mobile application 172 may be configured to receive messages from the enterprise system 110 and may be activated when not in use based on an SMS text message from the enterprise system 110 providing nutrition information the end user.

Logic operating through the application 172 may offer an interface to users showing calories consumed, calories burned, and calories remaining. Consumption may be based on the nutrition information provided by the enterprise 110. However, the user may have the opportunity to add or delete items consumed on a user interface presented by the mobile application 172. For example, the user may delete items that were purchased by the user but consumed by other person. The user may select and add items that were purchased by another person, but consumed by the user.

The application 172 may further include heuristics to operate in combination with the mobile device 170 to make recommendations to end users based on geo-location of the end user device 170. For example, the mobile application 172 operate in conjunction with a geo-location apparatus in order to determine a current end user location and may provide end users with products within a pre-set radius, for example, a five mile radius, of the current location. End users may further set one or more particular locations where they would like to locate a product or service. The logic of the application 172 may search for restaurants partnering with the enterprise 110 or accessible in the promotions database 154. The application 172 may make particular recommendations to users based on promotions, geolocation, and nutrition information.

The applications 172 may be downloadable from a web site provided by the enterprise 110. The mobile app 172 is downloadable over the Internet via a network interface to the subscriber mobile devices as described above. In embodiments of the invention, the end users visit an enterprise website using a browser application to download the mobile application 172. Once downloaded, the downloadable mobile application 172 may operate on the user mobile devices to interact with the enterprise system 110. The downloadable applications may also operate in conjunction with third party systems 160 and nutrition aggregator system 190.

Based on a request to access transaction receipt 165*a* from user device 170, integration module 150 may be operable to identify the requested transaction receipt 165*a*. For example, processor 151 of integration module 150 may analyze transaction receipts 165*a*-165*n* stored in receipts database 152 and identify transaction receipt 165*a* as the requested transaction receipt by distinguishing transaction receipt 165*a* from transaction receipts 165*b*-165*n*. In certain embodiments, integration module 150 is operable to communicate the requested transaction receipt (e.g, receipt 165*a*) to application 172 (e.g., application 172*a* on smartphone 170*a*, application 172*b* on laptop 170*b*, or application 172*c* on tablet 170*c*) on user device 170. For example, interface 158 of integration module 150 may receive a request from smartphone 170*a* to access a transaction receipt from a particular vendor. Processor 151 may identify the particular transaction receipt 165 from the receipts stored in receipts database 152, and interface 158 may communicate the requested transaction receipt 165 to application 172*a* on smartphone 170*a*. The user may then be able to quickly and efficiently access transaction receipt 165 from smartphone 170*a*. As will be further described below with respect to FIG. 1B, the integration module 150 may further communicate nutritional information to the user devices in response to a user request, or alternatively on a regularly scheduled basis.

As illustrated in the embodiment of FIG. 1A, transaction information received by integration module 150 may comprise one or more promotions 154. A promotion 154 is something given to a customer to raise customer awareness of a product, brand or service, to create brand loyalty, and/or to generate sales. Integration module 150 may electronically receive a promotion from third party 160 and store the promotion in promotions database 154. Promotions 154 received by integration module 150 may comprise coupons 166*a*-166*n* and/or rewards 168*a*-168*n*.

In some embodiments, processor 151 of integration module 150 is operable to generate rewards 156*a*-156*n* for customers of enterprise 110. Generated rewards 156 may be stored in promotions database 154. In certain embodiments, generated rewards 156 are based on the received transaction information. Integration module 150 may be further operable to communicate generated rewards 156 to an application (e.g., application 172) on a user device (e.g., smartphone 170*a*). For example, integration module 150 may receive transaction receipt 165 indicating that a customer of enterprise 110 spent 100 at third party 160 and charged the transaction amount to a credit card associated with customer account 122. In this example, processor 151 may generate reward 156*a* comprising 100 points in honor of the customer, wherein award 156*a* represents a point for every dollar charged by the customer to the credit card associated with customer account 122. Integration module 150 may then communicate generated reward 156*a* (i.e., 100 points) to application 172 on user device 170, which allows the customer to manage and access the points at the customer's convenience.

In certain embodiments, integration module 150 receives a request to access a promotion from user device 170, wherein the promotion may be associated with third party 160. Based on the request to access the promotion, processor 151 may be operable to identify the requested promotion from promotions stored in database 154. In some embodiments, interface 158 is operable to communicate the requested promotion to application 172 (e.g., application 172*a* on smartphone 170*a*, application 172*b* on laptop 170*b*, and application 172*c* on tablet 170*c*) on user device 170. For example, integration module 150 may receive a request from tablet 170*c* to access a coupon from a vendor. Integration module 150 may then identify the vendor's coupon from coupons 166*a*-166*n* stored in promotions database 154 and communicate the requested vendor's coupon to application 172*c* on tablet 170*c*. The user may then be able to quickly and efficiently access the vendor's coupon from tablet 170*c*.

In some embodiments, transaction information received by integration module 150 may be associated with temporary email address 142. For example, third party 160 may email transaction receipt 165 to temporary email address 142. Integration module 150 may intercept a copy of transaction receipt 165 when transaction receipt 165 is sent to temporary email address 142. As another example, third party 160 may email coupon 166 to temporary email address 142, and integration module 150 may intercept a copy of coupon 166 when coupon 166 is sent to temporary email address 142. As yet another example, third party 160 may email reward 168 (e.g., points) to temporary email address 142, and integration module 150 may intercept a copy of reward 168 when reward 168 is sent to temporary email address 142.

Logic 153 of integration module 150 may include one or more computer programs operable to parse out information from emails sent to temporary email address 142. The logic 153 may further include logic for parsing information received from third party nutrition aggregator 190. In certain embodiments, processor 151 may parse out data from an email sent to temporary email address 142 based on a template of an expected data structure. For example, processor 151 may identify transaction receipt 165 from an email sent to temporary email address 142 based on a template, and the identified transaction receipt 165 may be stored in receipts database 152. In some embodiments, processor 151 may parse out data per line item from an email sent to temporary email address 142. For example, processor 151 may parse out a line item for a health care expense or consumable item having nutritional value from transaction receipt 165 and store that particular health care or consumption expense in a sub folder of receipts database 152 that includes health related expenses or food consumption related expenses.

In certain embodiments, transaction module 130 is operable to complete the transaction in response to receiving the transaction information and communicate the completed transaction to third party 160. As an example, transaction module 130 receives a request from third party 160 to authorize a transaction for the purchase of an undetermined amount of gas for a customer of enterprise 110. Transaction module 130 authorizes the gas purchase transaction based on available funds in customer account 122, and temporary email generator 140 generates temporary email address 142 associated with the authorized transaction and communicates temporary email address 142 to third party 160. After third party 160 determines the cost for the gas received by the customer at third party 160, third party 160 may generate transaction receipt 165a and communicate transaction receipt 165a to enterprise 110. Enterprise 110 may then complete the transaction based on available funds in customer account 122 and communicate the transaction completion to third party 160. By requiring the receipt of transaction receipt 165a prior to completing the transaction, enterprise 110 may incentivize third party 160 to timely communicate transaction receipt 165 to enterprise 110.

According to some embodiments of the present disclosure, processor 151 of integration module 150 may be operable to determine, from the transaction information, an item purchased by a customer and determine a financial recommendation based on the purchased item and data from customer account 122. In certain embodiments, interface 158 of integration module 150 may be operable to communicate the financial recommendation to application 172 on user device 170. For example, processor 151 of integration module 150 may determine, from transaction receipt 165, that customer of enterprise 110 purchased a cup of coffee. Based on the purchased coffee, interface 158 of integration module 150 may communicate a financial recommendation to application 172c on tablet 170c, wherein the financial recommendation comprises transferring 2 from customer account 122a (i.e., customer savings account) to customer account 122b (i.e., customer checking account).

As another example, processor 151 of integration module 150 may determine, from transaction receipt 165, that customer of enterprise 110 invested in Stock A. Based on the purchased stock, interface 158 of integration module 150 may communicate a financial recommendation to application 172 that customer invest in Stock B. In certain embodiments, a customer account of enterprise 110 may comprise one or more rules that automatically generate a financial transaction based on information obtained by enterprise 110 from a transaction receipt. For example, a rule associated with customer account 122a may automatically transfer money from a customer's checking account to the customer's savings account when the transaction receipt shows a purchase of a certain class of items (e.g., clothing items).

Further, in embodiments of the invention, the processor 151 of the integration module may be operable to determine, from the transaction receipt 165, nutrition information associated with the purchases contained on the transaction receipt 165 through communication with the third party nutrition information aggregator 190. The processor 151 may further determine, through communication with a user mobile application 172 or through information stored by the user, recommendations for consuming other items based on the nutritional value of those items. The interface 158 may communicate these types of recommendations to end users 170 of the system. For example, the recommendations may include recommended alternatives to items purchased or an indication of remaining calories allowed based on stored goals and retrieved nutrition information.

In some embodiments, promotions database 154 is linked to customer account 122 such that a user of customer account 122 can search promotions database 154. For example, a user of customer account 122 may search receipts database 165 for expenses related to a certain category, such as health care expenses. The searchable database feature allows users to access records of certain expenses. In certain embodiments, a user may generate a financial transaction based on information obtained by enterprise 110 from the transaction information. For example, a customer may transfer funds to a savings account when transaction receipt 165 indicates a purchase of a certain class of items (e.g., household items). In some embodiments, enterprise 110 may offer incentives to a customer when the customer links customer account 122 to promotions database 154. Enterprise 110 may also provide information to the customer regarding other types of products or recommendations.

Network 180 may include any suitable one or more components for communicably coupling customer database 120, transaction module 130, temporary email generator 140, integration module 150, point-of-sale 162, memory 164, and user device 170. For example, network 180 may include an ad-hoc network, an intranet, an extranet, a virtual private network (VPN), a wired or wireless local area network (LAN), wide area network (WAN), metropolitan area network (MAN), a portion of the Internet, a portion of the Public Switched Telephone Network (PSTN), a portion of a cellular telephone network, or any other suitable communication link, including combinations thereof, operable to facilitate communication between the components of system 100. This disclosure contemplates end networks having one or more of the described properties of network 180.

System 100 includes one or more interfaces (e.g., interface 158). An interface represents any suitable device operable to receive information from network 180, transmit information through network 180, perform suitable processing of the information, communicate to other devices, or any combination of the preceding. For example, an interface of transaction module 130 may receive a request from third party 160 to authorize a transaction. As another example, interface 158 of integration module 150 may communicate temporary email address 142 to third party 160. Interfaces represent any port or connection, real or virtual, including any suitable hardware and/or software, including protocol conversion and data processing capabilities, to communicate through a LAN, WAN, or other communication system that allows enterprise 110 to exchange information between customer database 120, transaction module 130, temporary email generator 140, integration module 150, third party 160, user device 170, and other components of system 100.

In addition, system 100 includes one or more processors (e.g., processor 151). Processors control the operation and administration of enterprise 110 and/or the particular component by processing information received from interfaces. As such, processors are communicatively coupled to the interfaces. Processors include any hardware and/or software that operate to control and process information. For example, a processor of transaction module 130 generates a transaction identifier to identify a transaction. As another example, a processor of temporary email generator 140 generates temporary email address 142 for a transaction. In the illustrated embodiment, processor 151 facilitates the integration of the transaction information from various third parties 160. A processor may be programmable logic device, a microcontroller, a microprocessor, any suitable processing device, or any suitable combination of the preceding.

System 100 further includes one or more memories. For example, the illustrated embodiment of FIG. 1 includes memory 164 for third party 160, customer database 120, receipts database 152 and promotions database 154 in integration module 150. A memory may represent a database that stores, either permanently or temporarily, information associated with a customer, information associated with third party 160, or any other suitable information. Memory includes any one or a combination of volatile or non-volatile local or remote devices suitable for storing information. For example, memory may include Random Access Memory ("RAM"), Read-only Memory ("ROM"), magnetic storage devices, optical storage devices, or any other suitable information storage device or a combination of these devices. Memory may include any suitable information for use in the operation of enterprise 110. Additionally, memory may be a component external to enterprise 110 and may be situated in any location suitable for memory to communicate to the other modules of system 100. Each component of system 100 (e.g., transaction module 130 and third party 160) can each contain more than one memory.

One or more rules may be included in the one or more memories and/or the one or more processors. Rules generally refer to logic (e.g., 153), rules (e.g., rules 155), algorithms, code, tables, and/or other suitable instructions embodied in a computer-readable storage medium for performing the described functions and operations of system 100. For example, rules may facilitate the generation of temporary email address 142 based on transaction identifier 132. In the illustrated embodiment of FIG. 1, logic 153 and rules 155 of integration module 150, upon execution by processor 151, facilitate identifying requested transaction information and determining whether to communicate the requested transaction information to an application on a user device. Logic 153 and rules 155 may also facilitate determining a financial recommendation based on a purchased item and data from a customer account (e.g., customer account 122). Similarly, other components of system 100 may comprise logic and rules. For example, transaction module 130 may comprise logic and rules that facilitate authorizing a transaction and determining a transaction identifier (e.g., transaction identifier 132).

Rules 155 may facilitate in tracking transaction information. In some embodiments, rules 155 may track transaction information by identifying and grouping transaction information based on similar products. For example, rules 155 may identify food and beverage purchases from receipts database 152 and a memory of integration module 150 may store the food and beverage purchases in a sub folder of receipts database 152, wherein the food and beverage purchases are from different vendors. A user may then access the sub folder to track food and beverage purchases across different locations. Additionally, enterprise 110 may use information acquired from cross-location tracking to drive promotions (e.g., business promotions) and/or to bank specific products such as savings incentives and credits. Information acquired from cross-tracking may include the types of items purchased by a customer, the time of year the items were purchased, the locations the items were purchased, or any other information that may be useful to enterprise 110 for driving promotions or banking specific products.

In an exemplary embodiment of operation, enterprise 110 stores customer account 122 associated with a customer in customer database 120. In the illustrated embodiment, customer account 122 includes email address 124 of the customer. Third party 160 sends message 181 to network 180 to authorize a transaction, and enterprise 110 receives message 182 from network 180 requesting authorization. Transaction module 130 of enterprise 110 authorizes the transaction and generates, in response to the authorized transaction, transaction identifier 132 to identify the transaction. Temporary email generator 140 of enterprise 110 generates temporary email address 142 for the transaction in response to generated transaction identifier 132. Temporary email address 142 may be based on transaction identifier 132. In an embodiment, temporary email generator 140 links temporary email address 142 to customer email address 124 and communicates temporary email address 124 (e.g., message 183) to network 180. Third party 160 receives temporary email address 124 (e.g., message 184) from network 180 and sends the transaction information (e.g., message 181) to network 180. Integration module 150 of enterprise 110 receives the transaction information (e.g., message 182) from network 180 and stores the transaction information, wherein the transaction information is associated with temporary email address 124.

In another exemplary embodiment of operation, user device 170 sends a request (e.g., message 185) to network 180 to access transaction information (e.g., receipt 165, coupon 166, and/or reward 168). Integration module 150 of enterprise 110 receives the request to access transaction information from network 180, identifies the requested transaction information, and communicates the requested transaction information. User device 170 receives the requested transaction information (e.g., message 186) from network 180.

System 100 may include one or more computers. A computer may be any device that interacts with system 100. A computer may use a processor and a memory to execute an application in order to perform any of the functions described herein. A computer may be a personal computer, a workstation, a laptop, a wireless or cellular telephone, an electronic notebook, a personal digital assistant, a tablet, or any other device (wireless, wireline, or otherwise) capable of receiving, processing, storing, and/or communicating information with other components of system 100. A computer may also include a user interface, such as a display, a touchscreen, a microphone, keypad, or other appropriate terminal equipment usable by a user.

A component of system 100 may include an interface, logic, memory, and/or other suitable element. An interface receives input, sends output, processes the input and/or output, and/or performs other suitable operations. An interface may comprise hardware and/or software. Logic performs the operations of the component. For example, logic executes instructions to generate output from input. Logic may include hardware, software, and/or other logic. Logic may be encoded in one or more non-transitory, tangible media, such as a computer readable storage medium or any other suitable tangible medium, and may perform operations when executed by a computer. Certain logic, such as a processor, may manage the operation of a component. Examples of a processor include one or more computers, one or more microprocessors, one or more applications, and/or other logic.

Modifications, additions, or omissions may be made to system 100 of FIG. 1 without departing from the scope of the invention. For example, system 100 may include any number of customer databases 120, integration modules 150, third parties 160, and user devices 170. Similarly, customer database 120, as an example, may include a plurality of databases in some embodiments. In some instances, memory 164 may be external to third party 160. Furthermore, the components of system 100 may be integrated or separated. For example, transaction module 130 and integration module 150 may be incorporated into a single component. Additionally, a component of system 100 may be operable to perform a task of a different component of system 100. For instance, integration module 150 may be operable to link temporary email address 142 to customer email address 124.

Figure 1B:
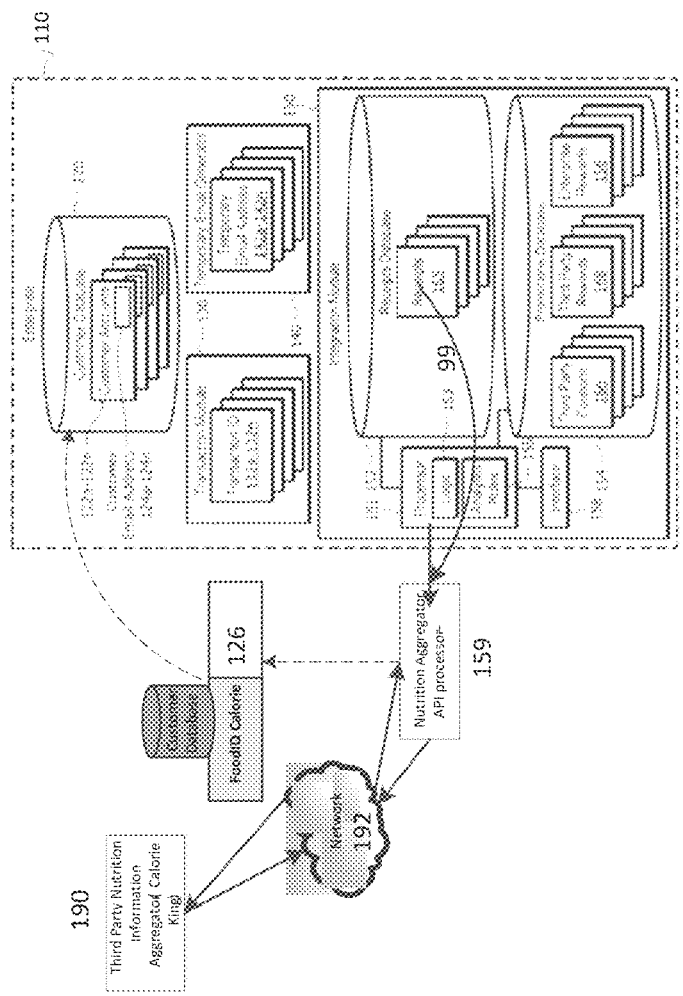
FIG. 1B is a work flow diagram illustrating operation of specific components of the system for providing nutrition information.

FIG. 1B includes a workflow diagram illustrating the collection, assembly, and distribution of nutrition information associated with a transaction in accordance with an embodiment of the invention. Like reference numerals represent like components with reference to FIG. 1A. In the illustrated embodiment, the logic 153 may utilize a nutrition logic processor 156 including one or more computer programs operable to communicate with the third party nutrition aggregator 190 leveraging nutrition aggregator API 159. In embodiments of the invention, the nutrition aggregator API 159 may be provided by the third party nutrition aggregator 190.

The nutrition logic processor 156 may include logic for extracting transaction information from receipts 165 and collecting nutrition information related to the transaction information over the network 192 from the third party nutrition aggregator system 190. Once the information is retrieved, the nutrition logic processor 156 may store the nutrition information in a customer nutrition record 126, which may be stored in the customer database 120. In embodiments of the invention, the collection of nutrition information may be triggered by use of a particular payment vehicle. For example, the enterprise 110 may be a financial institution and may provide a credit or debit card for use with the system described herein. Use of the payment vehicle may trigger identification of the consumable items and retrieval of the nutrition information.

For example, a retrieved transaction receipt 165 may indicate that a customer of the enterprise 110 spent one hundred dollars at the third party 160 and charged the transaction amount to a payment card, such as a credit card or debit card, associated with one of the customer accounts 122.

As set forth above, logic 153 of integration module 150 may include one or more computer programs operable to parse out information from emails sent to temporary email address 142. The processor 151 may parse out data per line item from an email sent to temporary email address 142. For example, process 151 may parse out a line item for a restaurant expense from transaction receipt 165 and store that particular restaurant expense line item in the database 152.

The nutrition logic processor 156 of the integration module 150 may include one or more computer programs operable to communicate with the third party nutrition information aggregator 190, e.g. CalorieKing™, Nutritionix™, etc. using the application program interface (API) 159 made available by the nutrition aggregator 190. The computer program of the nutrition logic processor 156 would make an API call to the aggregator system 190 over the network 192, (which may be the Internet) and receive nutrition information for a specific item 99 identified in the restaurant expense for receipt 165. The item 99 identified by logic 156 along with the name of the third party restaurant or other establishment 100 could then be used to request nutrition information from the aggregator service 190. An example is provided below.

For example, the item 99 may be determined to be a burger purchased at third party restaurant 100 called McDonalds®. To obtain nutrition information for the item 99, the nutrition logic processor 156 makes a request to the aggregator system 190 asking for information on all food types that match the food type of item 99. The parsing logic contained within integration module 150 may have capabilities to identify the type of food item e.g. burger and capabilities to identify the common name of the food item e.g. Big Mac Burger.

A sample call from the nutrition logic processor 156 may, for example, be in the following format:

GET/
    foods?query=burger&region=us&fields=Summary,mass

The third party nutrition aggregator 190 responds to the initial request with a list of all burgers available on the menu offered by third party 100, which in this case is McDonalds®. A sample response received from the nutrition information aggregator system 190 is provided below in Table 1:

TABLE 1

```
{
  "metadata"a":{
    "total": 5080,
    "limit": 20,
    "offset": 0
  }
  "foods":[
    {
      "revisionId": "4093fb31-bd3a-4100-9c9c-14106ba582fa",
      "brand": {
        "id": "c4697cb5-74b3-437a-a1cd-d663cabd4f9f",
        "name": "McDonald's"
      },
      "name": "Big Mac Burger",
      "classification": "Sandwiches & Burgers",
      "mass": 215.0
    },
    ...
  ]
}
```

As illustrated in Table 1, the response includes a revision ID, a brand ID and brand name, and an item name and classification. The response may be parsed by the nutrition logic processor 156 to identify the revisionId of the matching item. In this example, the matching item 99 happens to be Big Mac® Burger.

A second request to the nutrition aggregator system 190 using API 159 may be made to request additional information including nutrition and calorie data as shows below:

GET/foods/37216b92-fbea-4acd-9b43-e

79721d6c559?fields=$summary,tags/name/nutrition

The nutrition information aggregator 190 may return the information as shown in Table 2.

TABLE 2

```
{
  "food":{
    "revisionId": "4093fb31-bd3a-4100-9c9c-14106ba582fa",
    "brand": {
       "id": "c4697cb5-74b3-437a-a1cd-d663cabd4f9f",
       "name": "McDonald's"
    },
    "tags": [
      {
        "name": "Fast-Food Chains & Restaurants"
      },
      {
        "name": "Sandwich & Burger"
      },
      {
        "nutrients": [
          {
            "energy": "920"
            ...
          },
        ],
        "name": "Big Mac Burger",
        "classification": "Sandwiches & Burgers"
      }
    }
  }
```

The Java Script Object Notation (JSON) response key "energy" shown above provides the amount of calories in item number 99 which, in this embodiment, is a Big Mac® burger purchased at third party restaurant 100, which is in this case, McDonalds®. Additional nutrients such as Fat, Carbohydrate etc. can also be obtained using the above-described API structure.

Once the information is obtained and parsed by the nutrition logic processor 156, the information is stored in a new table 126 within the customer database 120. The new table 126 will have all the information to associate the customer ID to the transaction ID and eventually to the food item 99 and the nutrition information parsed from the receipt 165. This table 126 can then be connected to a customer statement and be presented alongside purchase history or in other forms.

In additional embodiments, the system 100 may display a dashboard of daily, monthly and weekly nutrition consumption. In embodiments of the invention, the dashboard may further display personal vs group expenses and thus add parameters indicative of personal vs group consumption to the system. A sample entry from the table 126 is shown in Table 3 below.

TABLE 3

| CustID | TransID | FoodItemID | NutKey | FoodCalorie | TransDate |
|---|---|---|---|---|---|
| 223223 | 455878 | 4093fb31-bd3a-4100-9c9c-14106ba582fa | Energy | 920 | May 23, 2016 |

Figure 2:
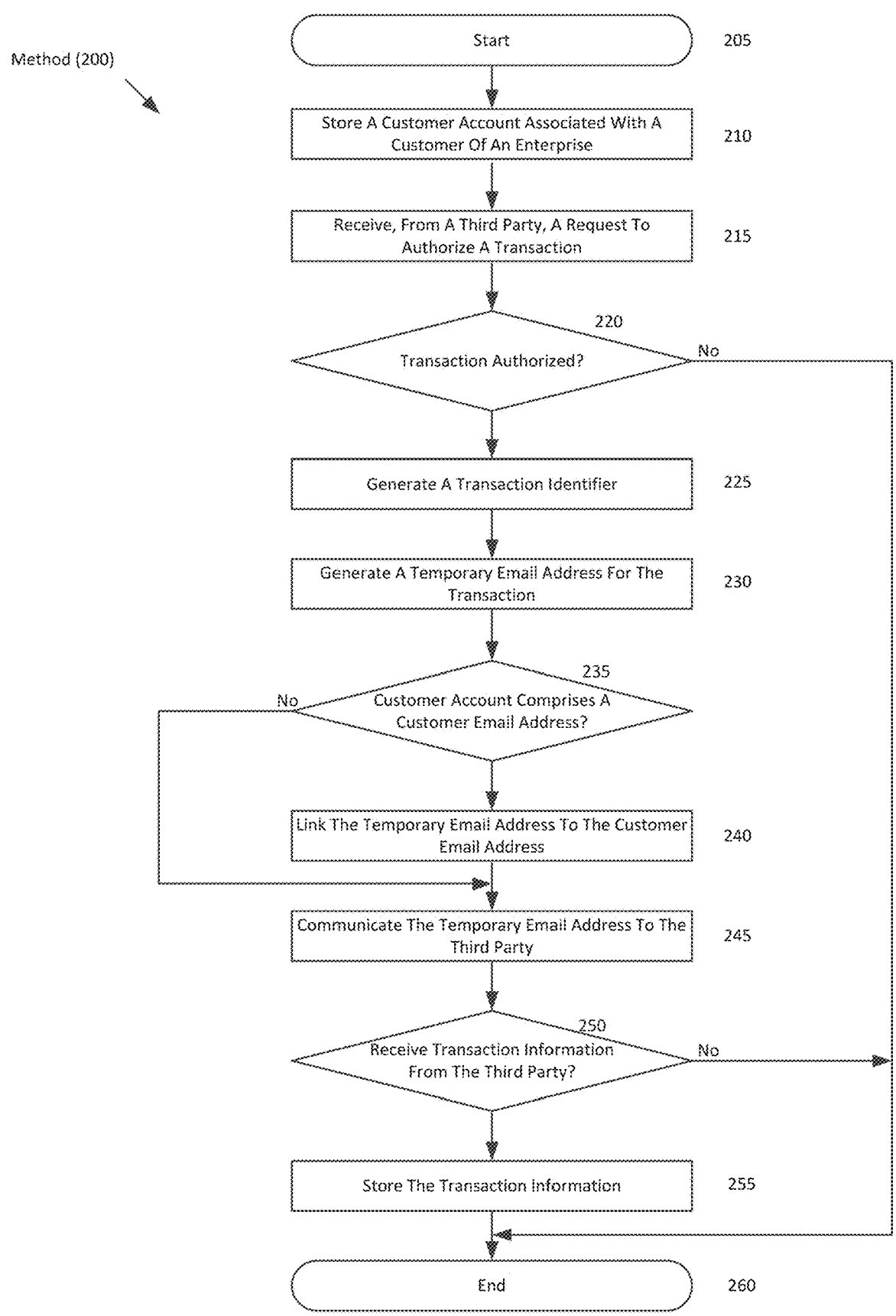
FIG. 2 is a flow diagram illustrating recording of a transaction in accordance with an embodiment of the invention.

FIG. 2 illustrates an example method 200 for transaction-based temporary email in accordance with embodiments of the present disclosure. The method starts at step 205. At step 210, a customer account (e.g., customer account 122) associated with a customer of an enterprise (e.g., enterprise 110) is stored in one or more memories. For example, the customer account may be stored in a customer database (e.g., customer database 120). In some instances, the customer account may be stored in a memory external to the enterprise. In some embodiments, the customer account comprises an email address of the customer.

At step 215, a request to authorize a transaction is received from a third party (e.g., third party 160). The transaction may be associated with a customer of the third party. The third party's customer may also be a customer of an enterprise (e.g., enterprise 110). At step 220, a processor determines whether the transaction is authorized. For example, a customer of an enterprise may have a customer account (e.g., customer account 122*a*) with the enterprise. The enterprise may receive a request to authorize a purchase transaction from a third party. In this example, the purchase transaction is between the customer of the enterprise and the third party.

The enterprise may then authorize the purchase transaction based on adequate funds in the customer account. Alternatively, if the customer account shows inadequate funds, the enterprise may deny authorization of the purchase transaction and method 200 moves to step 260, where the method ends. If it is determined that the transaction is authorized, method 200 proceeds to step 225. At step 225, a transaction identifier (e.g., transaction identifier 132*a*) is generated. The transaction identifier identifies the transaction and may be temporarily associated with a customer account. In some embodiments, the transaction identifier is a unique, temporary identifier that expires after a certain amount of time after the transaction is completed. The transaction identifier may be recycled and reused for a future transaction. In some embodiments, the transaction identifier is not recycled and may be permanently associated with a customer account.

At step 230, a temporary email address (e.g., temporary email address 142*a*) is generated for the transaction. The temporary email address may be based on the generated transaction identifier. For example, a processor may generate a temporary email address by incorporating the transaction identifier into the local part of the temporary email address. In some instances, the local part of the temporary email address may consist entirely of the transaction identifier. For example, if the generated transaction identifier is 123abc456, the generated temporary email address may be 123abc456@domain.com. In some embodiments, temporary email address may not be based on the transaction identifier.

At step 235, a determination is made as to whether the customer account comprises an email address of the customer. If it is determined that the customer account comprises a customer email address, method 200 moves to step 240, where the temporary email address is linked to a customer email address. As an example, an enterprise links the temporary email address to the customer email address by mapping the temporary email address to the customer email address. As another example, the enterprise may link the temporary email address to the customer email address by automatically forwarding emails received by the temporary email address to the customer email address. If it is determined that the customer account does not comprise a customer email address, the method skips step 240 and advances to step 245.

At step 245, the temporary email address is communicated to the third party. For example, an enterprise may communicate the temporary email address to the third party over a network (e.g., network 180). At step 250, a processor determines whether transaction information (e.g., transaction receipt 165, coupon 166, and/or reward 168) is received from the third party. For example, the third party may communicate a transaction receipt to the enterprise using the temporary email address communicated to the third party, and the enterprise may receive the transaction receipt through an email associated with the temporary email address. If it is determined that transaction information is received from the third party, the transaction information is stored at step 255. For example, the enterprise may store a received transaction receipt in a receipt database (e.g., receipt database 152). After storing the transaction information, the method ends at step 260. If it is determined that transaction information is not received from the third party, method 200 skips step 255 and advances to step 260, where the method ends.

Figure 3:
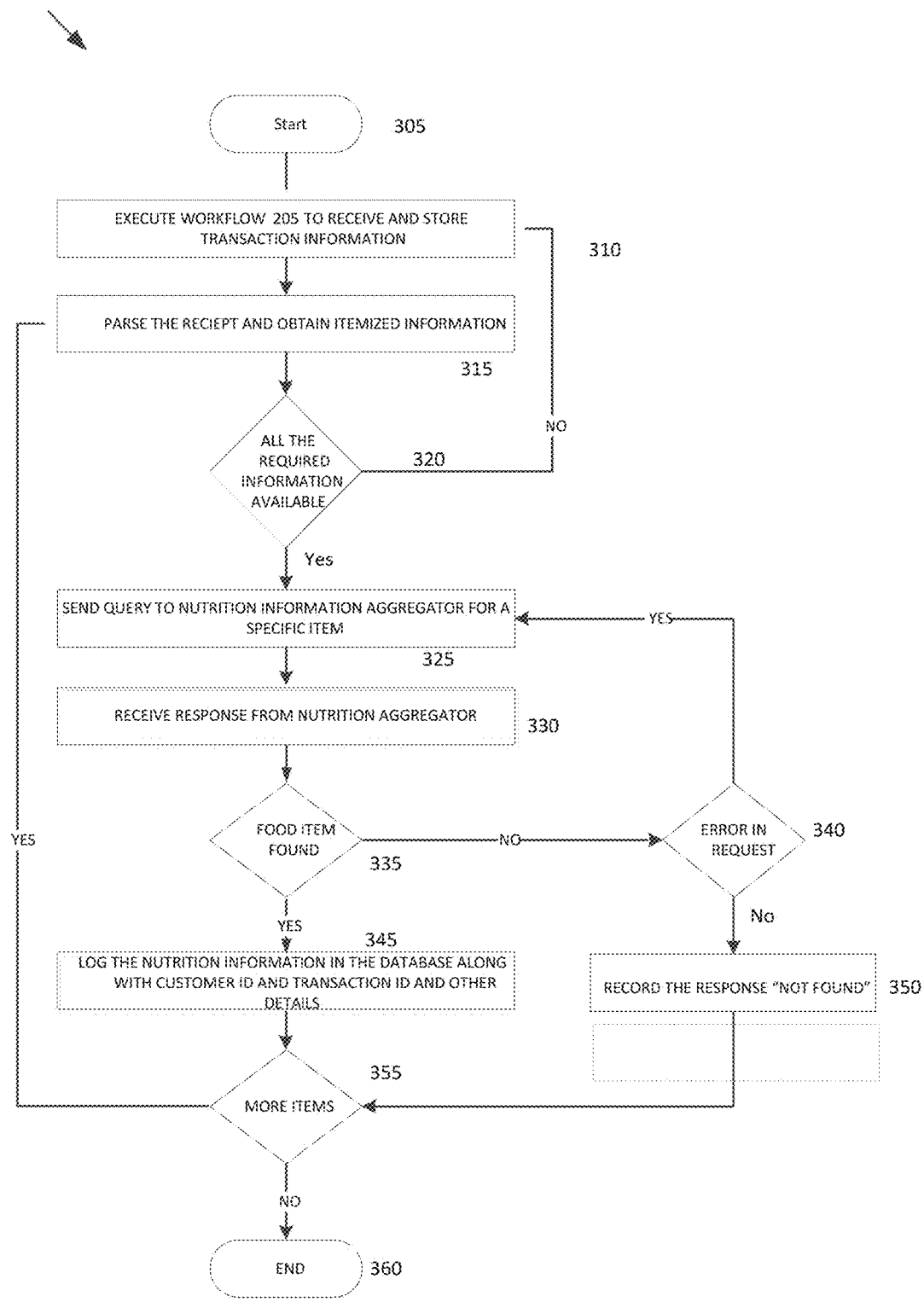
FIG. 3 is a flow chart illustrating a process for obtaining nutrition information based on received transaction information in accordance with an embodiment of the invention.

FIG. 3 illustrates a nutrition information processing method 300 that may be utilized in conjunction with the workflow of FIG. 2. The method starts at 305 and the enterprise system executes the workflow 205 shown in FIG. 2 at step 310. At step 315, the enterprise system parses the receipt obtained through the workflow 205 to obtain itemized transaction information. In step 320, the enterprise system determines if all of the required information is available from the received receipt. If the required information is unavailable in step 320, the system returns to the workflow 205.

If the required information is available in step 320, the system, through the nutrition logic processor 156 and API 159 sends a query to the nutrition information aggregator for a specific item. As set forth above, the query may, for example, take the following form:

```
GET/
    foods?query=burgers&region=us&fields=$summary,mass
```

In step 330, the enterprise system receives a response from the nutrition aggregator system. The response may, for example, take the form of Table 1 shown above. In step 335, the enterprise system determines if the food item was found by the nutrition aggregator table based on the content of the response. If no corresponding food item is found in step 335, the system may review the original request in step 340 to determine if an error was present. If an error was present, the system may return to step 325 and revise the query and send the revised query. If no error was found in step 340, the system may record the response as "not found" in step 350 and return to determine if more items should be retrieved from the transaction receipt in step 355. Further, as set forth above with respect to FIG. 1B, the logic 156 may make multiple calls and receive multiple responses from the nutrition aggregator system 190 in order to ensure that all required nutrition information is received and stored.

If a food item is found in step 335, the system reviews the response from the nutrition aggregator and logs the nutrition information in the database in step 345 along with the customer ID, transaction ID, and other details contained within the transaction receipt. In step 355, the system determines if the transaction receipt includes more items and returns to step 315 to parse the receipt if more items are present. If no more items are present, the process ends in step 360.

Figure 4:
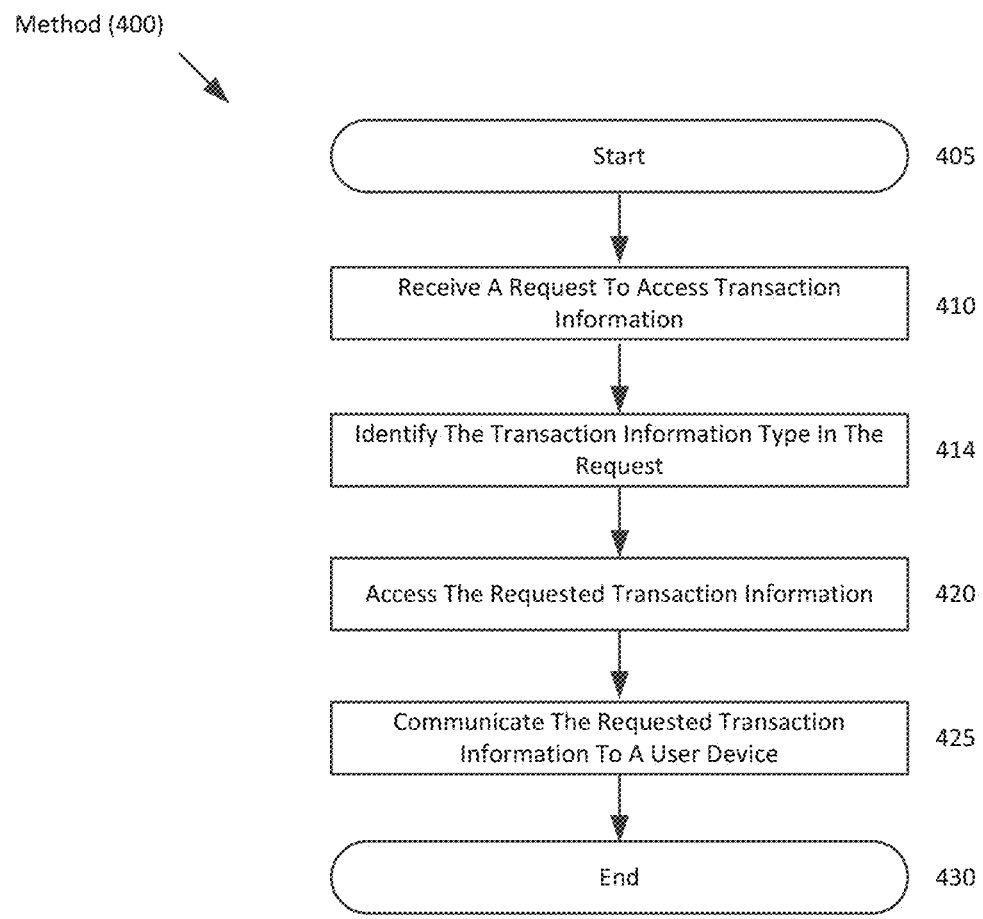
FIG. 4 is a flow chart illustrating a process of responding to a user request for transaction information in accordance with an embodiment of the invention.

FIG. 4 illustrates an example method 400 for transmitting transaction information to an end user in accordance with an embodiment of the invention. The method starts at step 405. At step 410, a request to access transaction information is received. The request may additionally include a request for nutrition information integrated with the transaction information. For example, an interface may receive a request to access transaction information (e.g., receipts 165, coupons 166, and/or rewards 168) from a user device (e.g., user device 170). Method 400 next moves to step 415, where the transaction information type in the request is identified. For instance, a processor may determine that the requested transaction information type is a receipt 165. At step 420, the requested transaction information is accessed. In some embodiments, a processor accesses the transaction information. Method 400 then moves to step 425, where the requested transaction information is communicated to a user device. For example, an enterprise may receive a request from a smartphone (e.g., smartphone 170*a*) of a customer of the enterprise to access a coupon. The enterprise identifies the coupon from the coupons in the enterprise's promotion database and communicates the coupon to the customer's smartphone, which allows the customer to quickly and efficiently access the coupon. After communicating the transaction information to the user device, method 400 ends at step 430.

In embodiments of the invention, the customer may request access to nutrition information in step 410. This request may be a one-time request for nutritional information obtained during a pre-determined time period in the past, or may alternatively be a standing request for transmission of nutrition information as it is acquired. In the former instance, the system receives the request in step 410, uses its logic 156 to search for nutrition information for items obtained during the predetermined time period, and transmits the nutrition information to the end user device 170. In the latter instance, on an ongoing basis after receiving the request, the enterprise system 110 seeks nutrition information from the nutrition aggregator system 190 for every receipt including items for consumption. The nutrition information is transmitted to the customer database 120 to be stored in a customer record 126 as set forth above and is periodically transmitted to the end user device 170. The transmission may occur at a particular time daily or weekly or may be triggered by a particular event, such as, for example, a user entry into a mobile application 172.

The end user may utilize a mobile application 172 offered by the enterprise system 110, the nutrition aggregator system 190, or other entity to track nutrition information. The mobile app may optionally offer nutrition tracking in conjunction with energy expenditure tracking, and may monitor the relationship of these parameters to goals pre-set by the end user. Alternatively, a fitness tracker with its own applications may be utilized by the end user.

When the system transmits information daily, the mobile app or fitness tracker may operate so as to inform the user how many calories the user can still consume during a particular day in order to meet pre-specified goals.

In embodiments of the invention, the system may transmit an SMS text message to the user containing the calorie consumption information. The SMS text message may interact with and activate the mobile application in order to convey additional information to the user, such as remaining calories, and nutritional recommendations based on the pre-set goals. These SMS messages alerts can be received by the end user mobile device when the end user is offline and bring the end user online through selection of the text message or information, such as a URL contained in the text message. The URL may, for example reference the nutrition information displayed on a website hosted by the enterprise system.

Figure 5:
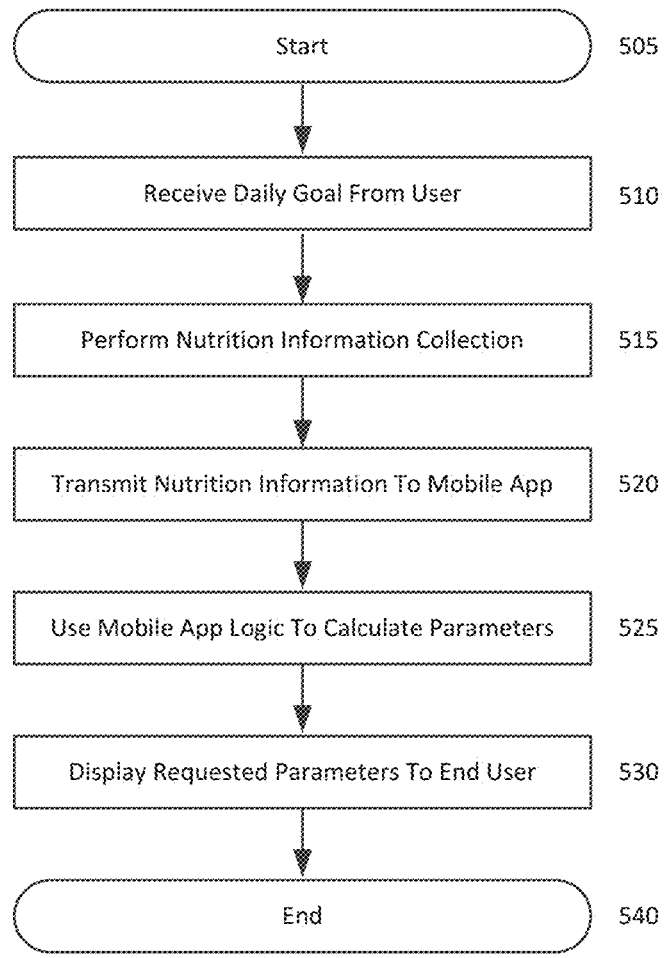
FIG. 5 is a flow chart illustrating use of a mobile application for conveying nutrition information to an end user in accordance with an embodiment of the invention.

FIG. 5 is a flow chart illustrating use of a mobile application for conveying nutrition information to an end user in accordance with an embodiment of the invention. As set forth above, the end user device 170 may include the mobile application 172 for operating on nutrition information received from the enterprise system 110. Method 500 starts in step 505 and the mobile application 172 receives a goal from the user in step 510. The goal may, for example, be a daily calorie consumption goal. Alternatively, the goal may be a net calorie loss goal. In step 515, the system 110 performs nutrition information collection, which may occur periodically, such as daily, or may alternatively occur in real time. For example, the mobile application, when used for banking in addition to nutrition tracking, may cause the transaction receipts to be generated based on purchases made utilizing the mobile app 172. Nutrition information collection may be triggered by these purchases.

In step 515, the enterprise system 110 collects nutrition information in a manner consistent with the steps shown in FIG. 3. In step 520, the enterprise system 110 transmits the collected nutrition information (collected in accordance with the steps shown in FIG. 3) to the mobile application 172. The transmission may occur periodically, at a time designated by the user, such as at 5 PM every day. The transmission may alternatively occur in real time.

In step 525, the mobile application 172 stored on the user device 170 calculates parameters for display to the end user. For example, the mobile application 172 may access a stored calorie intake goal for the day and subtract the total calorie count received in the transmitted nutrition information from the calorie intake goal. The mobile application 172 may thus calculate the remaining calories available for consumption within the pre-set goal. Other parameters, such as calories burned, may be taken into account to perform calculations known in the art.

In step 530 the mobile app 172 may display calculated parameters to the end user on the end user device 170. The mobile app 172 may also display promotions available in the current vicinity of the end user based on user location parameters.

Modifications, additions, or omissions may be made to methods 200, 300, 400, and 500 without departing from the scope of the present disclosure. For example, the order of the steps may be performed in a different manner than that described and some steps may be performed at the same time. Additionally, each individual step may include additional steps without departing from the scope of the present disclosure.

Certain embodiments of the present disclosure may provide one or more technical advantages. A technical advantage of one embodiment includes generating a temporary email address for a transaction associated with a customer and communicating the temporary email address to a third party (e.g., a vendor). This may eliminate the need for the customer to enter a personal email address when making a transaction, which saves the customer time. Also, by not entering a personal email address, the customer reduces privacy concerns. Another technical advantage may include receiving transaction information (e.g., a transaction receipt) from a third party and storing the transaction information, which may eliminate the need for customers to maintain paper receipts.

As another example, a technical advantage may include providing a single application that allows a user to access transaction information (e.g., a transaction receipt and nutrition information) associated with multiple vendors. Using this application, a user requests the transaction information using a user device, the requested transaction information is identified, and the requested transaction receipt is communicated to the application on the user device. This technique facilitates a quick and efficient retrieval of the transaction information from a plurality of vendors using the single application. Another technical advantage of an embodiment includes providing a central repository for rewards and coupons for multiple vendors, and allowing a customer to access the rewards and/or coupons and nutrition information through an application on a user device. A further technical advantage of an embodiment of the present disclosure includes determining a financial recommendation based on a purchase item and data from a customer account, which may assist customers in managing their customer accounts.

It should also be readily apparent to one of ordinary skill in the art that the presently disclosed invention may be implemented in a wide range of industries. Although the present disclosure includes several embodiments, changes, substitutions, variations, alterations, transformations, and modifications may be suggested to one skilled in the art, and it is intended that the present disclosure encompass such changes, substitutions, variations, alterations, transformations, and modifications as fall within the spirit and scope of the appended claims.

From the foregoing, it will be seen that this invention is one well adapted to attain all the ends and objects set forth above, together with other advantages, which are obvious and inherent to the system and method. It will be understood that certain features and sub-combinations are of utility and may be employed without reference to other features and sub-combinations. This is contemplated and within the scope of the appended claims.

The invention claimed is:

1. A nutrition monitoring and communication system for communicating nutritional data to end user devices, the system comprising:
   at least one communication interface for receiving data from external sources including merchant systems distributing items having nutritional value and a third party aggregator system storing nutritional information for the distributed items;
   at least one computer memory storing instructions and databases storing receipts transmitted from the merchant systems, each receipt associated with a customer operating an end user device, wherein the receipts include an identification of the distributed items;
   at least one computer processor accessing the computer memory and executing the instructions to perform steps including:
      calling an application program interface of the aggregator system and providing data from identified receipts including identification of distributed items that includes an item identifier and a third party establishment name;
      receiving nutrition information for the distributed items from the aggregator system;

parsing the received nutrition information that includes
identifying a revision ID associated with the distributed item; and storing the parsed nutrition information including the received nutrition information with a customer ID, a transaction ID, and a transaction date in a customer database stored in the computer memory for communication to the end user devices; and generating a temporary email address by incorporating the transaction ID into a local part of the temporary email address;

monitoring a certain amount of time that the transaction ID is valid after the transaction is completed, wherein passing of the certain amount of time resulting in the transaction ID becoming expired;

recycling the expired transaction II) after passing of the certain amount of time and using the same recycled transaction ID at a later time to identify a different authorized transaction;

automatically transferring, based on rules associated with a customer account, money from customer's checking account to customer's savings account when the receipt associated with the customer operating the end user device shows a purchase of a certain class of items; and determining whether the customer account associated with the customer operating the end user device includes a customer email address;

when it is determined that the customer account includes the customer email address, linking the temporary email address to the customer email address, automatically forwarding emails received by the temporary email address to the customer email address, and communicating the temporary email address to the third party aggregator system; and when it is determined that the customer account does not include a customer email address, communicating the temporary email address to the third party aggregator system; and a mobile application operating on the end user devices to communicate information received from the nutrition monitoring and communication system to a user of the end user devices, wherein a user interface displayed on the mobile application is configured to receive a user input to delete an item that was purchased by the user of the end user devices but consumed by another person, wherein the user interface displayed on the mobile application is configured to receive a user input to add an item that was purchased by another person but consumed by the user, wherein the data provided from the identified receipts includes a transaction data that includes a promotion associated with a third party related with the third party aggregator system, the third party promotion comprises a coupon or a reward, and the at least one computer processor is further configured to execute the instructions to perform the following:

receiving a request to access, from the end user device and via a communication network, the promotion;

identifying the promotion responsive to the request with the customer account; and communicating the promotion to the mobile application on the end user device via the communication network.

2. The system of claim 1, further comprising a communication interface, wherein collection of the nutrition infou iation through the communication interface is triggered by use of a particular payment vehicle.

3. The system of claim 1, wherein the computer processor transmits an SMS text message to the mobile application on the end user device, the SMS text message including access to the nutrition information.

4. The system of claim 1, wherein the mobile application receives user consumption goals and tracks user consumption in relation to the user consumption goals.

5. The system of claim 1, further comprising calling the application program interface to request additional nutrition information for the distributed item.

6. The system of claim 1, wherein the nutrition information comprises fat and carbohydrate information.

7. A method for monitoring and communicating nutritional data to end user devices, the method comprising:

receiving data from external sources including merchant systems distributing items having nutritional value and a third party aggregator system storing nutritional information for the distributed items;

storing instructions and databases in at least one computer memory, the databases including a receipts database storing receipts transmitted from the merchant systems, each receipt associated with a customer operating an end user device, wherein the receipts include an identification of the distributed items;

accessing the computer memory and executing the instructions using at least one computer processor to perform steps including:

calling an application program interface of the aggregator system and providing data from identified receipts including identification of distributed items that includes an item identifier and a third party establishment name;

receiving nutrition information for the distributed items from the aggregator system;

parsing the received nutrition information that includes identifying a revision ID associated with the distributed item; and storing the parsed nutrition information including the received nutrition information with a customer ID, a transaction ID, and a transaction date in a customer database stored in the computer memory for communication to the end user devices;

generating a temporary email address by incorporating the transaction ID into a local part of the temporary email address;

monitoring a certain amount of time that the transaction ID is valid after the transaction is completed, wherein passing of the certain amount of time resulting in the transaction ID becoming expired;

recycling the expired transaction ID after passing of the certain amount of time and using the same recycled transaction ID at a later time to identify a different authorized transaction;

automatically transferring, based on rules associated with a customer account, money from customer's checking account to customer's savings account when the receipt associated with the customer operating the end user device shows a purchase of a certain class of items; and determining whether the customer account associated with the customer operating the end user device includes a customer email address;

when it is determined that the customer account includes the customer email address, linking the temporary email address to the customer email address, automatically forwarding emails received by the temporary email address to the customer email address, and communicating the temporary email address to the third party aggregator system; and when it is determined that the customer account does not include a customer email address, communicating the temporary email address to the third party aggregator system;

utilizing a mobile application operating on the end user devices to communicate information received from a nutrition monitoring system to a user of the end user devices;

receiving a user input via a user interface displayed on the mobile application to delete an item that was purchased by the user of the end user devices but consumed by another person; and receiving a user input via the user interface displayed on the mobile application to add an item that was purchased by another person but consumed by the user, wherein the data provided from the identified receipts includes a transaction data that includes a promotion associated with a third party related with the third party aggregator system, the third party promotion comprises a coupon or a reward, and the at least one computer processor is further configured to execute the instructions to perform the following:

receiving a request to access, from the end user device and via a communication network, the promotion;

identifying the promotion responsive to the request with the customer account; and communicating the promotion to the mobile application on the end user device via the communication network.

8. The method of claim 7, further comprising transmitting an SMS text message to the mobile application on the end user device, the SMS text message including access to the nutrition information including calories per distributed item.

9. The method of claim 8, further comprising receiving at the mobile application receives, user consumption goals, and tracking through the mobile application, user consumption in relation to the user consumption goals.

10. The method of claim 7, further comprising calling the application program interface to request additional nutrition information for the distributed item, wherein the nutrition information comprises fat and carbohydrate information.

11. A non-transitory computer-readable medium storing instructions executed by a computer processor to perform steps including:

receiving data from external sources including merchant systems distributing items having nutritional value and a third party aggregator system storing nutritional information for the distributed items;

storing instructions and databases in at least one computer memory, the databases including a receipts database storing receipts transmitted from the merchant systems, each receipt associated with a customer operating an end user device, wherein the receipts include an identification of the distributed items;

calling an application program interface of the aggregator system and providing data from identified receipts including identification of distributed items that includes an item identifier and a third party establishment name;

receiving nutrition information for the distributed items from the aggregator system;

parsing the received nutrition information that includes identifying a revision ID associated with the distributed item; and storing the parsed nutrition information including the received nutrition information with a customer ID, a transaction ID, and a transaction date in a customer database stored in the computer memory for communication to the end user devices;

generating a temporary email address by incorporating the transaction ID into a local part of the temporary email address;

monitoring a certain amount of time that the transaction ID is valid after the transaction is completed, wherein passing of the certain amount of time resulting in the transaction ID becoming expired;

recycling the expired transaction ID after passing of the certain amount of time and using the same recycled transaction ID at a later time to identify a different authorized transaction;

automatically transferring, based on rules associated with a customer account, money from customer's checking account to customer's savings account when the receipt associated with the customer operating the end user device shows a purchase of a certain class of items; and determining whether the customer account associated with the customer operating the end user device includes a customer email address;

when it is determined that the customer account includes the customer email address, linking the temporary email address to the customer email address, automatically forwarding emails received by the temporary email address to the customer email address, and communicating the temporary email address to the third party aggregator system; and when it is determined that the customer account does not include a customer email address, communicating the temporary email address to the third party aggregator system;

utilizing a mobile application operating on the end user devices to communicate information received from a nutrition monitoring system to a user of the end user devices, receiving a user input via a user interface displayed on the mobile application to delete an item that was purchased by the user of the end user devices but consumed by another person; and receiving a user input via the user interface displayed on the mobile application to add an item that was purchased by another person but consumed by the user, wherein the data provided from the identified receipts includes a transaction data that includes a promotion associated with a third party related with the third party aggregator system, the third party promotion comprises a coupon or a reward, and the computer processor is further configured to execute the instructions to perform the following:

receiving a request to access, from the end user device and via a communication network, the promotion;

identifying the promotion responsive to the request with the customer account; and communicating the promotion to the mobile application on the end user device via the communication network.

12. The non-transitory computer-readable medium of claim 11, wherein the mobile application includes heuristics to operate in combination with the end user devices, wherein the instructions, when executed, causes the computer processor to further perform:

providing a recommendation to the user of the end user devices based on determining a current location of the user of the end user devices and providing products on the user interface displayed on the mobile application that are available within a pre-set radius of the current location.

13. The system of claim 1, wherein the mobile application includes heuristics to operate in combination with the end user devices to provide a recommendation to the user of the end user devices based on determining a current location of the user of the end user devices and providing products on the user interface displayed on the mobile application that are available within a pre-set radius of the current location.

14. The method of claim 7, wherein the mobile application includes heuristics to operate in combination with the end user devices, the method further comprising:

providing a recommendation to the user of the end user devices based on determining a current location of the user of the end user devices and providing products on the user interface displayed on the mobile application that are available within a pre-set radius of the current location.

* * * * *